US012644735B2

(12) United States Patent
Aljuaydi et al.

(10) Patent No.: US 12,644,735 B2
(45) Date of Patent: Jun. 2, 2026

(54) DETERMINING HYDROCARBON RESERVOIR PRODUCTION WITH A MINIATURE MULTI-PHASE FLOWMETER

(71) Applicant: Saudi Arabian Oil Company, Dhahran (SA)

(72) Inventors: Haitham Aljuaydi, Kharj (SA); Yazeed Alamro, Riyadh (SA)

(73) Assignee: Saudi Arabian Oil Company, Dhahran (SA)

( * ) Notice: Subject to any disclaimer, the term of this patent is extended or adjusted under 35 U.S.C. 154(b) by 198 days.

(21) Appl. No.: 18/465,562

(22) Filed: Sep. 12, 2023

(65) Prior Publication Data

US 2025/0085144 A1      Mar. 13, 2025

(51) Int. Cl.
   *G01F 1/44*      (2006.01)
   *E21B 47/10*     (2012.01)
   *G01N 27/06*    (2006.01)
   *G01N 33/28*    (2006.01)

(52) U.S. Cl.
   CPC ............... *G01F 1/44* (2013.01); *E21B 47/10* (2013.01); *G01N 27/06* (2013.01); *G01N 33/2823* (2013.01)

(58) Field of Classification Search
   CPC ...... G01F 1/44; G01N 33/2823; G01N 33/28; G01N 27/06
   See application file for complete search history.

(56) References Cited

U.S. PATENT DOCUMENTS

| | | | |
|---|---|---|---|
| 6,935,189 B2 * | 8/2005 | Richards ................... | G01F 1/74 73/861.04 |
| 7,934,433 B1 * | 5/2011 | Franco ................... | G01F 7/005 73/861.63 |
| 2011/0040485 A1 * | 2/2011 | Ong ......................... | G01F 1/74 702/12 |

(Continued)

OTHER PUBLICATIONS

Agar, "New Coriolis Based Multiphase Flow Meter For Heavy Oil Mature Fields," Prepared for presentation at the 2010 SPE Russian Oil & Gas Technical Conference and Exhibition held in Moscow, Russia, Oct. 26-28, 2010, 12 pages.

(Continued)

*Primary Examiner* — Kristina M Deherrera
*Assistant Examiner* — Jean F Morello
(74) *Attorney, Agent, or Firm* — Fish & Richardson P.C.

(57) ABSTRACT

A method and a system for determining hydrocarbon reservoir production with a coiled tubing having a miniature multi-phase flowmeter. Deploying the miniature multi-phase flowmeter in the wellbore by the coiled tubing orients the miniature multi-phase flowmeter in a wellbore extending to a hydrocarbon reservoir containing a multi-phase reservoir fluid. The miniature multi-phase flowmeter has a venturi oriented in along a longitudinal axis of the coiled tubing and multiple sensors. The multi-phase reservoir fluid is conducted from the wellbore through the coiled tubing to the miniature multi-phase flowmeter. The venturi and sensors sense conditions including a pressure, a differential pressure, a temperature, a bulk fluid flow rate, an electrical capacitance, and an electrical conductance of the multi-phase reservoir fluid. Based on the conditions of the multi-phase reservoir fluid, a production condition of the hydrocarbon reservoir is determined.

15 Claims, 3 Drawing Sheets

(56) References Cited

U.S. PATENT DOCUMENTS

2019/0330971 A1 * 10/2019 Xiao ....................... E21B 47/06

OTHER PUBLICATIONS

Al-Shuwaikhat et al., "Optimizing Production Facilities Using None-Radio Active Source MPFM in Ghawar Field in Saudi Aramco," Prepared for presentation at the SPE Saudi Arabia section Young Professionals Technical Symposium held in Dhahran, Saudi Arabia, Mar. 29-30, 2008, 18 pages.

* cited by examiner

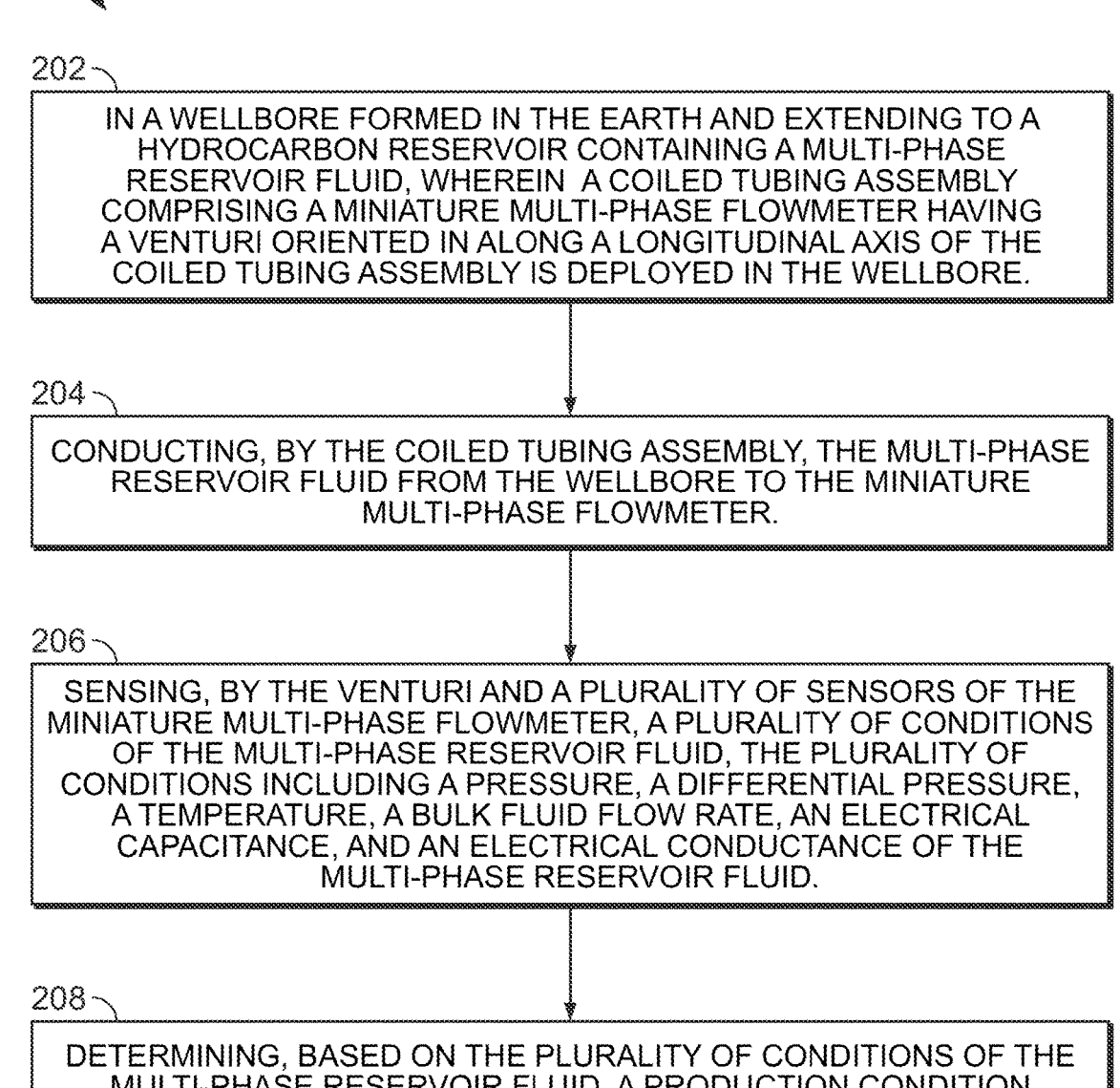

200

202
IN A WELLBORE FORMED IN THE EARTH AND EXTENDING TO A HYDROCARBON RESERVOIR CONTAINING A MULTI-PHASE RESERVOIR FLUID, WHEREIN A COILED TUBING ASSEMBLY COMPRISING A MINIATURE MULTI-PHASE FLOWMETER HAVING A VENTURI ORIENTED IN ALONG A LONGITUDINAL AXIS OF THE COILED TUBING ASSEMBLY IS DEPLOYED IN THE WELLBORE.

204
CONDUCTING, BY THE COILED TUBING ASSEMBLY, THE MULTI-PHASE RESERVOIR FLUID FROM THE WELLBORE TO THE MINIATURE MULTI-PHASE FLOWMETER.

206
SENSING, BY THE VENTURI AND A PLURALITY OF SENSORS OF THE MINIATURE MULTI-PHASE FLOWMETER, A PLURALITY OF CONDITIONS OF THE MULTI-PHASE RESERVOIR FLUID, THE PLURALITY OF CONDITIONS INCLUDING A PRESSURE, A DIFFERENTIAL PRESSURE, A TEMPERATURE, A BULK FLUID FLOW RATE, AN ELECTRICAL CAPACITANCE, AND AN ELECTRICAL CONDUCTANCE OF THE MULTI-PHASE RESERVOIR FLUID.

208
DETERMINING, BASED ON THE PLURALITY OF CONDITIONS OF THE MULTI-PHASE RESERVOIR FLUID, A PRODUCTION CONDITION OF THE HYDROCARBON RESERVOIR.

FIG. 2

DETERMINING HYDROCARBON RESERVOIR PRODUCTION WITH A MINIATURE MULTI-PHASE FLOWMETER

TECHNICAL FIELD

This disclosure relates to determining hydrocarbon reservoir production, particularly, with a coiled tubing assembly having a miniature multi-phase flowmeter.

BACKGROUND

Wellbores in an oil and gas well receive and flow fluids from sub-surface formations of the Earth and conduct fluids to a surface of the Earth. The fluids can include both liquid and gaseous phases of various fluids and chemicals including water and hydrocarbon liquids and gases. The fluids can include particulates and solid components. A coiled tubing assembly can be disposed in the wellbore to conduct the water and hydrocarbon liquids and gases to the surface. The production flow rate of the sub-surface formations can be determined. Sometimes, the multi-phase fluid with particulates can decrease an accuracy of the determined production flow rates.

SUMMARY

This disclosure describes technologies related to methods for determining hydrocarbon reservoir production. Hydrocarbon production can be determined with a miniature multi-phase flowmeter having a venturi oriented in along a longitudinal axis of the coiled tubing assembly is deployed in the wellbore. The coiled tubing assembly can orient the miniature multi-phase flowmeter in the wellbore such that the multi-phase reservoir fluid flows through the miniature multi-phase flowmeter in a vertical direction relative to a surface of the Earth.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

FIG. 2 is a flow chart of an example method of determining hydrocarbon reservoir production with a coiled tubing assembly and a miniature multi-phase flowmeter.

DETAILED DESCRIPTION

The present disclosure relates to determining hydrocarbon reservoir production with a coiled tubing assembly having a miniature multi-phase flowmeter. The miniature multi-phase flowmeter is coupled to a coiled tubing assembly. The coiled tubing assembly with the miniature multi-phase flowmeter is deployed in a wellbore fluidly coupled to the hydrocarbon reservoir. The hydrocarbon reservoir contains a reservoir fluid. The reservoir fluid is conducted from the wellbore through the coiled tubing assembly to the miniature multi-phase flowmeter. The reservoir fluid passes through the miniature multi-phase flowmeter. The miniature multi-phase flowmeter determines a condition of the reservoir fluid. Based on the condition of the reservoir fluid determined by the miniature multi-phase flowmeter, a production condition of the hydrocarbon reservoir is determined.

Implementations of the present disclosure realize one or more of the following advantages. Hydrocarbon reservoir production analysis can be improved. For example, hydrocarbon production from the reservoir can be determined without separating the reservoir fluid into its constituent components. For example, hydrocarbon reservoir production conditions can be determined in a live well when the coiled tubing assembly with the miniature multi-phase flowmeter is positioned in the wellbore. For example, a venturi of the miniature multi-phase flowmeter can pass sticky portions of the reservoir fluid which can clog and/or impede certain fluid sensors, such as spinners, improving hydrocarbon reservoir production analysis.

Monitoring of hydrocarbon reservoirs can be improved. For example, the coiled tubing assembly with the miniature multi-phase flowmeter can transmit the live conditions of the reservoir fluid flowing through the coiled tubing assembly to a user, for example, in a control center.

Figure 1A:
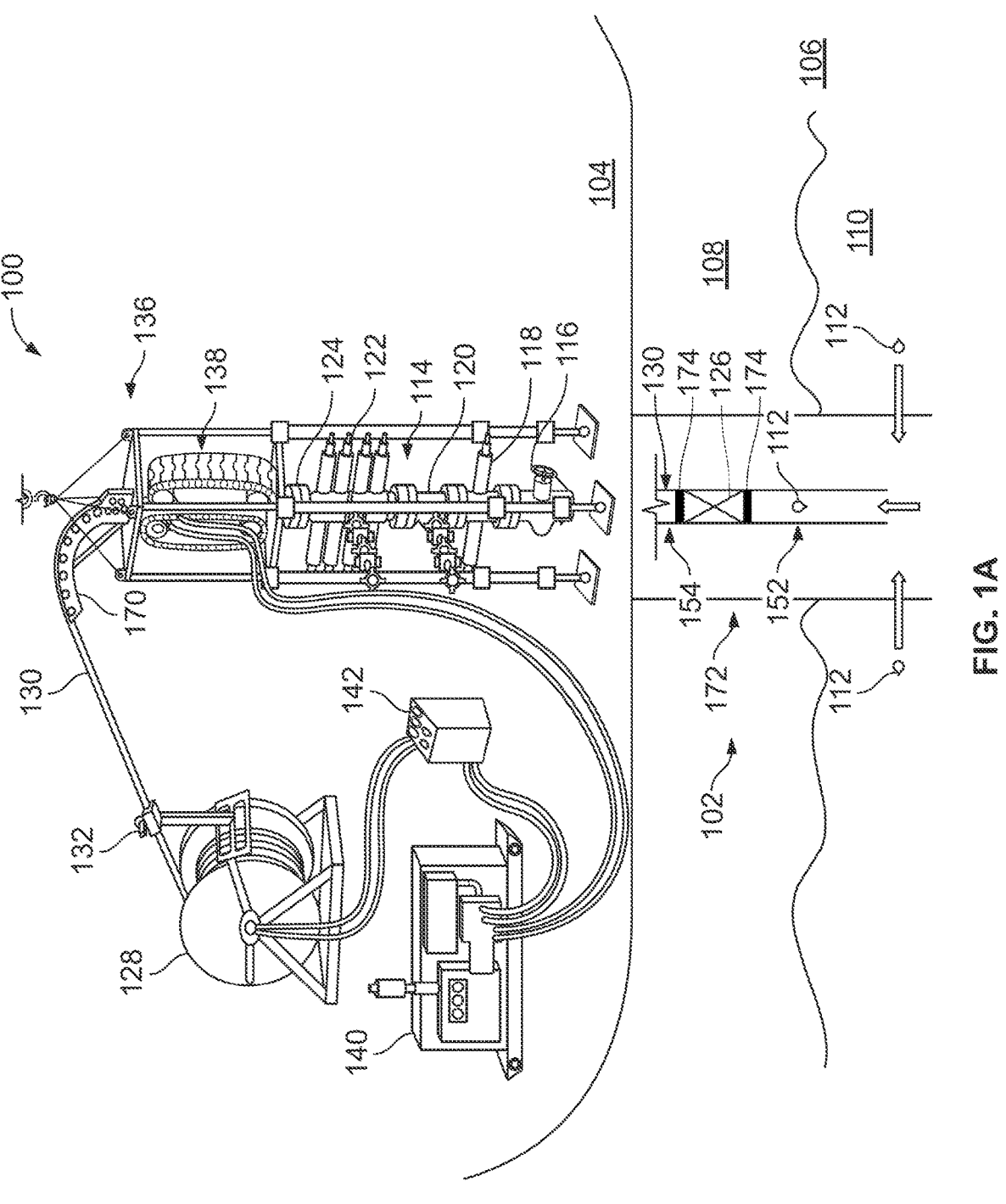
FIG. 1A is a schematic view of a coiled tubing assembly having a miniature multi-phase flowmeter positioned in a wellbore.
Figure 1B:
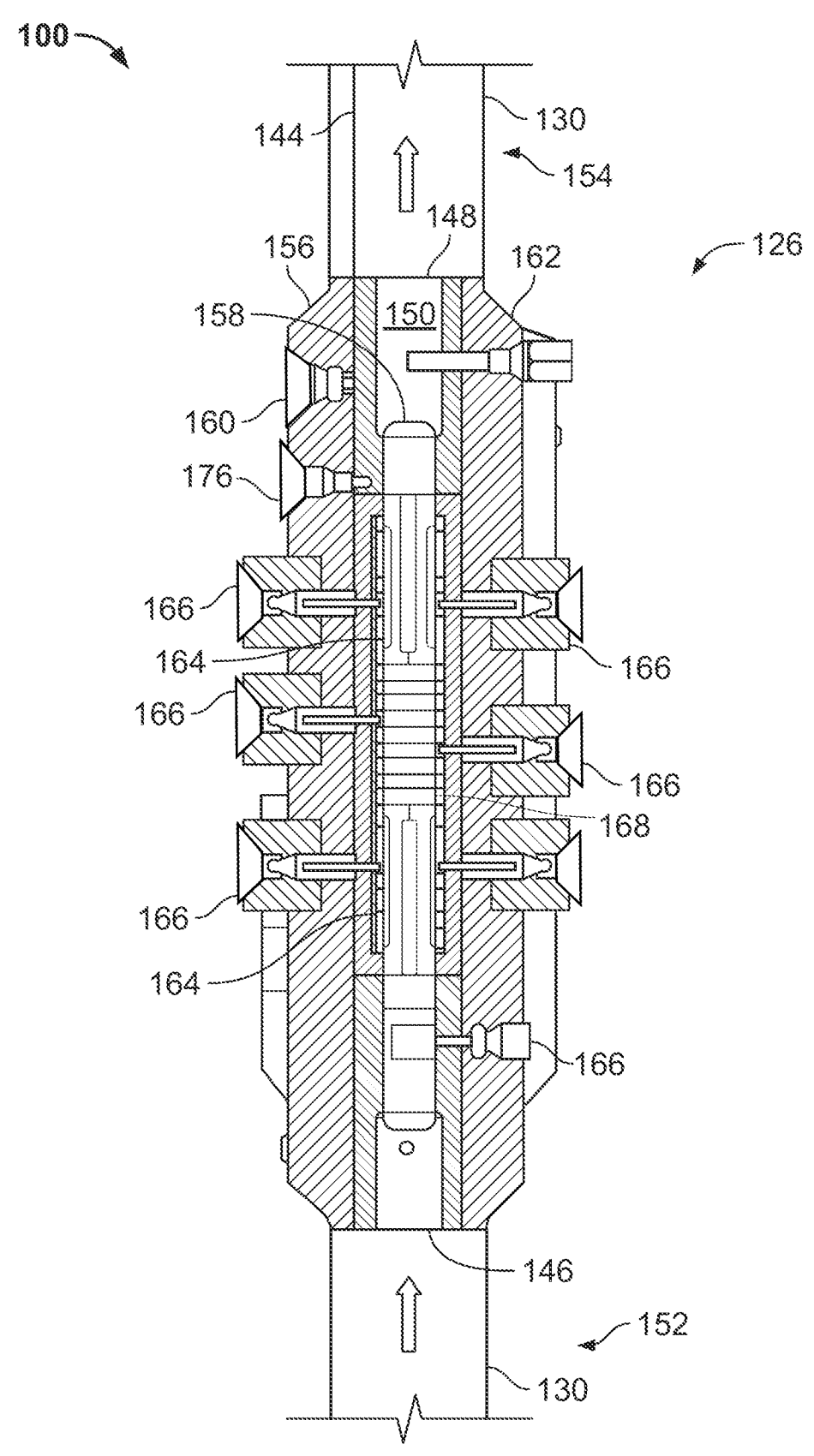
FIG. 1B is a schematic view of the miniature multi-phase flowmeter of FIG. 1A.

FIGS. 1A-1B show a system for determining hydrocarbon reservoir production. FIG. 1A is a schematic view of a coiled tubing assembly having a miniature multi-phase flowmeter positioned in a wellbore. FIG. 1B is a schematic view of the miniature multi-phase flowmeter. Referring to FIG. 1A, a coiled tubing assembly 100 with a miniature multi-phase flowmeter 126 (described in more detail in reference to FIG. 1B) is positioned in a wellbore 102 which extends from a surface 104 of the Earth 106 through the formations 108 of the Earth 106. Some of the formations 108 are a hydrocarbon reservoir 110 containing reservoir fluids 112. The wellbore 102 conducts reservoir fluids 112 (liquids and gases such as hydrocarbons and water) from the formations 108 of the Earth 106 to the surface 104 of the Earth 106. The reservoir fluid 112 can contain multiple phases (i.e., both liquids and gases) of the hydrocarbons and water. The coiled tubing assembly 100 can be disposed into the wellbore 102 to remove reservoir fluids 112 from the hydrocarbon reservoir 110 and transport the reservoir fluids 112 to the surface 104.

A wellhead assembly 114 is coupled to the wellbore 102 to seal the reservoir fluids 112 in the wellbore 102, to control the flow of reservoir fluids 112 from the wellbore 102, and to permit entry of completion tools, such as the coiled tubing assembly 100, into the wellbore 102. The wellhead assembly 114 has a wellhead valve 116 to open up and shut off flow and access to the wellbore 102 from a space outside the wellhead assembly 114 above the surface 104 of the Earth 106, a pipe ram 118 to seal the reservoir fluids 112 in the wellbore 102 either automatically in an emergency or by command, a flow tee 120 to direct reservoir fluid 112 flow, a well control stack sub-assembly 122, and a stripper sub-assembly 124 to seal against the coiled tubing assembly 100 when the coiled tubing assembly 100 is positioned through the wellhead assembly 114.

The coiled tubing assembly 100 includes a reel 128 positioned on the surface 104 of the Earth 106 and a coiled tubing tube 130 wrapped about the reel 128. The reel 128 is-hydraulically operated to deploy and retrieve the coiled tubing tube 130 into and from the wellbore 102 through the wellhead assembly 114. The coiled tubing assembly 100 includes a counter 132 to measure and determine a length of coiled tubing tube 130 extended or retrieved from the reel 128. The coiled tubing assembly 100 includes a stand 134 having injector support legs 136 structurally supporting a hydraulic drive tubing injector 138 which provides motive force to the coiled tubing tube 130 to move the coiled tubing tube 130 into and out of the wellbore 102 from the reel 128. The stand 134 includes a tubing guide arch 170 from the reel 128 into the stand 134. The coiled tubing assembly 100 includes a prime mover 140, such as a hydraulic pump (to flow hydraulic fluid to a hydraulic motor on the reel 128) or an electric motor to rotate the reel 128 and operate the hydraulic drive tubing injector 138 to move the coiled tubing tube 130. The coiled tubing tube 130 orients the miniature multi-phase flowmeter 126 vertically in the wellbore 102.

The miniature multi-phase flowmeter 126 measures the production fluid rate by obtaining the pressure drop across a venturi 158 (described in more detail below) created by the fluid passing through the venturi 158. To create this pressure drop, there needs to be a difference in elevations between the two pressure readings across the venturi 158. The two pressure readings are read by built-in differential pressure sensors 166 (described below in more detail) contained within the miniature multi-phase flowmeter 126. Thus, the more vertically oriented relative to the surface 104 the miniature multi-phase flowmeter 126 is positioned, the greater the difference in the two elevations of the differential pressure sensors 166, leading to more accurate readings and improved identification of the fluid phases of the multi-phase produced fluid.

The coiled tubing tube 130 can be run into a vertical section 172 of the wellbore 102 with the miniature multi-phase flowmeter 126 installed inside of the coiled tubing tube 130 with a flow inlet 146 (described in more detail below) facing towards a downhole end 152, which is the same direction of the coiled tubing tube 130 while running in hole into the wellbore 102. As the coiled tubing tube 130 enters the wellhead assembly 114 and continues going deeper into the wellbore 102, it will be facing in the downward direction toward the downhole end 152 and descending into the wellbore 102. The flow inlet 146 and the miniature multi-phase flowmeter 126 will be oriented by the coiled tubing tube 130 by being physically installed and coupled to the coiled tubing tube 130 and oriented in the vertical section 172 of the wellbore 102.

The coiled tubing assembly 100 includes a controller 142 operatively coupled to the prime mover 140 and the reel 128 to move the coiled tubing tube 130 into and out of the wellbore 102. Moving the coiled tubing tube 130 changes a position of the miniature multi-phase flowmeter 126 relative to the wellbore 102 and within the wellbore 102. The controller 142 transmits command signals to the reel 128, the prime mover 140, the hydraulic drive tubing injector 138, and the miniature multi-phase flowmeter 126. The controller 142 receives signals representing conditions of the reel 128, the prime mover 140, and the hydraulic drive tubing injector 138 from sensors (not shown) on the reel 128, the prime mover 140, and the hydraulic drive tubing injector 138. The controller 142 receives signals representing conditions of the wellbore and the reservoir fluid 112 as the reservoir fluid 112 passes through the miniature multi-phase flowmeter 126 when the miniature multi-phase flowmeter 126 is positioned in the wellbore 102.

The controller 142, based on the received signals representing the conditions of the wellbore and the reservoir fluid 112, determines the production of the reservoir fluid 112 from the hydrocarbon reservoir 110. The controller 142 receives signals representing a pressure, a temperature, a capacitance, a fluid flow rate, and an electrical conductance of the reservoir fluid 112 in the miniature multi-phase flowmeter 126. Based on the received signals representing the conditions of the reservoir fluid 112 in the miniature multi-phase flowmeter 126, the controller 142 calculates the total volume (WC %), mass of a multi-phase produced fluid with the ratio of each phase (i.e, gas/oil ratio (GOR) or ratio of produced gas to produced oil), a water-in-liquid ratio (WLR), and a gas volume fraction (GVF). The controller 142 then calculates, based on these initial outputs, oil, water, and gas volume flowrates, that is, the production rates of the reservoir fluid 112 from the hydrocarbon reservoir 110. The controller 142 receives these signals, plus the specific gravity and density of the reservoir fluid 112 passing through the venturi 158 of the miniature multi-phase flowmeter. Having received all these signals and data, the controller 142 processes the data and signals with a combination of fluid dynamics analysis, fluid properties analysis, and pressure-volume-temperature properties and formulas such as Bernoulli's formula to determine the production rates.

The coiled tubing assembly 100 includes a power and signal cable 144 (shown in FIG. 1B) extending through the coiled tubing tube 130 electrically coupled between the controller 142 and the miniature multi-phase flowmeter 126 to transmit command signals to the miniature multi-phase flowmeter 126 and to receive status signals and signals representing the conditions of the reservoir fluid 112 in the miniature multi-phase flowmeter 126 from the miniature multi-phase flowmeter 126. Additionally, the power and signal cable 144 conducts power from the controller 142 to the miniature multi-phase flowmeter 126.

Referring to FIG. 1B, the miniature multi-phase flowmeter 126 is coupled to the coiled tubing tube 130. The miniature multi-phase flowmeter 126 has a flow inlet 146 and a flow outlet 148 with a void 150 extending from the flow inlet 146 to the flow outlet 148 to conduct the reservoir fluid 112 from the flow inlet 146 to the flow outlet 148. The flow inlet 146 of the miniature multi-phase flowmeter 126 is positioned at a downhole end 152 (shown in both FIGS. 1A and 1B) of the coiled tubing tube 130 and the flow outlet 148 is positioned at an uphole end 154 (shown in both FIGS. 1A and 1B) of the coiled tubing tube 130. The downhole end 152 of the coiled tubing tube 130 receives the reservoir fluid 112 from the wellbore 102 and conducts the reservoir fluid 112 to the flow inlet 146 of the miniature multi-phase flowmeter 126. The uphole end 154 of the coiled tubing tube 130 receives the reservoir fluid 112 from the miniature multi-phase flowmeter 126 and conducts the reservoir fluid 112 to the surface 104.

The miniature multi-phase flowmeter 126 has a cylindrical body 156. The cylindrical body 156 is coupled to the uphole end 154 and the downhole end 152 of the coiled tubing tube 130. The miniature multi-phase flowmeter 126 can be installed in the coiled tubing tube 130 and held in-place using a coupler 174. For example, the coupler 174 can be a Zenith plug or a Y-Tool (Y-Block) plug. The coupler 174 prevents fluid circulation around the miniature multi-phase flowmeter 126 inside the coiled tubing tube 130. The coupler 174 can be a circular seal directing the reservoir fluid 112 from the coiled tubing tube 130 into the flow inlet 146 of the miniature multi-phase flowmeter 126 facing the downhole end 152 and from the flow outlet 148 facing the uphole end 154 back into the coiled tubing tube 130 and eventually produced up to the surface 104.

The miniature multi-phase flowmeter 126 includes multiple sensors positioned in the cylindrical body 156. The sensors sense conditions of the reservoir fluid 112 within the void 150 of the miniature multi-phase flowmeter 126 as the reservoir fluid 112 flow through the miniature multi-phase flowmeter 126 from the flow inlet 146 to the flow outlet 148. The sensors are electrically coupled to the power and signal cable 144 to receive electrical power from the controller 142 and transmit the status signals and the signals representing the conditions of the reservoir fluid 112 to the controller 142. The sensors include a venturi 158, a pressure sensor 160, a temperature sensor 162, one or more capacitance sensors 164, differential pressure sensors 166, and a conductance sensor 168.

The venturi 158 measures a flow rate of the reservoir fluid 112. The venturi 158 can be used in with the differential pressure sensor 166 as described in reference to the differential pressure sensor 166 to measure the flow rate of the reservoir fluid 112 when the reservoir fluid 112 is in a multi-phase condition, for example, when the reservoir fluid 112 is in both a liquid and gas phase. The venturi 158 can increase the accuracy of the measurement of differential pressure and flow rate of the reservoir fluid 112 even when the reservoir fluid 112 contains a quantity of solids. For example, solids such as sludge can sometimes clog or impede other types of flow rate sensors, which may still can pass through the venturi 158. The venturi 158 is positioned within the cylindrical body 156. The venturi 158 is positioned within the void 150 of the cylindrical body 156 between the flow inlet 146 and the flow outlet 148. The reservoir fluid 112 flows through the venturi 158 from the flow inlet 146 to the flow outlet 148 and is the flow rate of the reservoir fluid 112 is measured. The venturi 158 is positioned vertically in the wellbore 102 by the coiled tubing tube 130. Spinners use the principle of fluid segregation to measure flow rate because water is heavier than oil which is heavier than gas. Using this principle and spinners only works to measure flow rate in horizontal section of the wellbore 102. Spinners may not be reliable in the vertical section 172 where the different phases of the multi-phase reservoir fluid 112 moving upward to the surface 104 and mixed in together, as opposed to the horizontal sections where multi-phase reservoir fluids 112 are segregated by gravity assembling layers of gas, oil, and water in the wellbore 102. On the other hand, in the vertical section 172, the miniature multi-phase flowmeter 126 can identify the phases fractions and fluid compositions without the multi-phase reservoir fluid 112 being separated into layers.

The pressure sensor 160 extends through the cylindrical body 156. The pressure sensor 160 senses a pressure of the reservoir fluid 112 in the miniature multi-phase flowmeter 126. The pressure sensor 160 transmits a signal representing the pressure of the reservoir fluid 112 in the miniature multi-phase flowmeter 126 to the controller 142 by the power and signal cable 144.

The temperature sensor 162 extends through the cylindrical body 156. The temperature sensor 162 senses a temperature of the reservoir fluid 112 in the miniature multi-phase flowmeter 126. The temperature sensor 162 transmits a signal representing the temperature of the reservoir fluid 112 in the miniature multi-phase flowmeter 126 to the controller 142 by the power and signal cable 144.

The one or more capacitance sensors 164 are positioned within the void 150 between the cylindrical body 156 and the venturi 158. The capacitance sensors 164 sense an electrical capacitance of the reservoir fluid 112 in the miniature multi-phase flowmeter 126. The capacitance sensors 164 transmits a signal representing the electrical capacitance of the reservoir fluid 112 in the miniature multi-phase flowmeter 126 to the controller 142 by the power and signal cable 144. The capacitance sensors 164 measure the permittivity of the multi-phase reservoir fluid 112. The values of permittivity measured by the capacitance sensors 164 can be compared to threshold values of oil, water, and gas permittivity.

The differential pressure sensors 166 extends through the cylindrical body 156 and into the void 150 about and into the venturi 158. The differential pressure sensors 166 senses a differential pressure of the reservoir fluid 112 across the venturi 158 in the miniature multi-phase flowmeter 126. The differential pressure sensor 166 transmits a signal representing the differential pressure of the reservoir fluid 112 in the miniature multi-phase flowmeter 126 to the controller 142 by the power and signal cable 144.

The conductance sensor 168 is positioned within the void 150 between the cylindrical body 156 and the venturi 158. The conductance sensor 168 senses an electrical conductance of the reservoir fluid 112 in the miniature multi-phase flowmeter 126. The conductance sensor 168 transmits a signal representing the electrical conductance of the reservoir fluid 112 in the miniature multi-phase flowmeter 126 to the controller 142 by the power and signal cable 144.

The miniature multi-phase flowmeter 126 includes a greasing port 176. The greasing port 176 passes and supplies grease into the void 150 to lubricate and maintain the miniature multi-phase flowmeter 126.

FIG. 2 is a flow chart of an example method of determining hydrocarbon reservoir from hydrocarbon production. At 202, in a wellbore formed in the Earth and extending to a hydrocarbon reservoir containing a multi-phase reservoir fluid, a coiled tubing assembly having a miniature multi-phase flowmeter with a venturi oriented in along a longitudinal axis of the coiled tubing assembly is deployed in the wellbore. For example, the coiled tubing assembly 100 positions the coiled tubing with the miniature multi-phase flowmeter 126 in the wellbore 102. The reservoir fluid 112 flows from the hydrocarbon reservoir 110 into the wellbore 102 and into the downhole end 152 of the coiled tubing tube 130. The hydrocarbon reservoir 110 flows through the downhole end 152 of the coiled tubing tube 130 to the miniature multi-phase flowmeter 126.

At 204, the multi-phase reservoir fluid, by the coiled tubing assembly, is conducted from the wellbore to the miniature multi-phase flowmeter. For example, the reservoir fluid 112 flows into the miniature multi-phase flowmeter 126 from the flow inlet 146 to the flow outlet 148 by the coiled tubing tube 130.

At 206, conditions of the multi-phase reservoir fluid including a pressure, a differential pressure, a temperature, a bulk fluid flow rate, an electrical capacitance, and an electrical conductance of the multi-phase reservoir fluid are sensed by the venturi and multiple sensors of the miniature multi-phase flowmeter. For example, the venturi 158, the pressure sensor 160, the temperature sensor 162, the one or more capacitance sensors 164, the differential pressure sensors 166, and the conductance sensor 168 sense the conditions of the reservoir fluid 112 and transmit signals representing the conditions to the controller 142.

At 208, based on the conditions of the multi-phase reservoir fluid, a production condition of the hydrocarbon reservoir is determined. In some cases, the production condition includes one or more of a water-in-liquid ratio or a gas volume fraction. In some cases, based on the production condition, a production flow rate is determined. In some cases, the production flow rate includes at least one of an oil flow rate, a water flow rate, or a gas volume flowrate. In some implementations, the method includes transmitting the condition of the reservoir fluid to a controller on a surface of the Earth and receiving the condition of the reservoir fluid at the controller. For example, the controller 142 receives and calculates the water-in-liquid ratio, the gas volume fraction, a production flow rate is determined.

In some implementations, the method further includes supplying electrical power to the miniature multi-phase flowmeter. For example, the controller 142 transmits electrical power via the power and signal cable 144 to the miniature multi-phase flowmeter 126.

In some implementations, the method further includes orienting the miniature multi-phase flowmeter in the wellbore such that the reservoir fluid flows through the miniature multi-phase flowmeter in a vertical direction. For example, the coiled tubing assembly 100 vertically orients the miniature multi-phase flowmeter 126 vertically in the wellbore 102.

Embodiments

In an example aspect, a production condition of the hydrocarbon reservoir is determined. In a wellbore formed in the Earth and extending to a hydrocarbon reservoir containing a multi-phase reservoir fluid, a coiled tubing assembly having a miniature multi-phase flowmeter with a venturi oriented in along a longitudinal axis of the coiled tubing assembly is deployed in the wellbore. The multi-phase reservoir fluid from the wellbore is conducted by the coiled tubing assembly to the miniature multi-phase flowmeter. Multiple conditions of the multi-phase reservoir fluid are sensed by the venturi and a multiple sensors of the miniature multi-phase flowmeter. The conditions include a pressure, a differential pressure, a temperature, a bulk fluid flow rate, an electrical capacitance, and an electrical conductance of the multi-phase reservoir fluid. Based on the conditions of the multi-phase reservoir fluid a production condition of the hydrocarbon reservoir is determined.

In an example aspect combinable with any other example aspect, determining the condition of the multi-phase reservoir fluid by the electrical conductance includes determining a permittivity of the multi-phase reservoir fluid; comparing the permittivity of the multi-phase reservoir fluid to a threshold oil permittivity threshold, a water permittivity threshold, and a gas permittivity threshold; and based on a result of the comparison, determining the electrical the electrical conductance of the multi-phase reservoir fluid.

In an example aspect combinable with any other example aspect, the production condition includes one or more of a water-in-liquid ratio or a gas volume fraction.

In an example aspect combinable with any other example aspect, based on the production condition includes determining a production flow rate.

In an example aspect combinable with any other example aspect, the production flow rate includes at least one of an oil flow rate, a water flow rate, or a gas volume flowrate.

In an example aspect combinable with any other example aspect, determining the production condition of the hydrocarbon reservoir includes transmitting values representing the conditions of the multi-phase reservoir fluid to a controller on a surface of the Earth and receiving the values representing the conditions of the multi-phase reservoir fluid at the controller.

In an example aspect combinable with any other example aspect, determining the production condition of the hydrocarbon reservoir includes supplying electrical power to the miniature multi-phase flowmeter.

In an example aspect combinable with any other example aspect, determining the production condition of the hydrocarbon reservoir includes orienting the miniature multiphase flowmeter in the wellbore such that the multi-phase reservoir fluid flows through the miniature multi-phase flowmeter in a vertical direction relative to a surface of the Earth.

In another example aspect, a wellbore production system includes a wellhead, a coiled tubing assembly, a miniature multiphase flow meter, and a controller. The wellhead is coupled to a wellbore fluidly coupled to a hydrocarbon reservoir containing a multi-phase reservoir fluid. The coiled tubing assembly extends through the wellhead into the wellbore and flow the multi-phase reservoir fluid from wellbore to a surface of the Earth. The miniature multi-phase flowmeter is coupled to the coiled tubing assembly and positionable in the wellbore by the coiled tubing assembly. The miniature multi-phase flowmeter includes a venturi oriented in along a longitudinal axis of the coiled tubing assembly. The miniature multi-phase flowmeter senses conditions of the multi-phase reservoir fluid and transmits a signal representing the conditions of the multi-phase reservoir fluid. The conditions include a pressure, a differential pressure, a temperature, a bulk fluid flow rate, an electrical capacitance, and an electrical conductance of the multi-phase reservoir fluid. The controller performs operations including receiving a signal representing the conditions of the multi-phase reservoir fluid from the miniature multi-phase flowmeter; and determining, based on the conditions of the multi-phase reservoir fluid, a production condition of the hydrocarbon reservoir.

In an example aspect combinable with any other example aspect, the miniature multi-phase flowmeter includes at least one of a pressure sensor, a differential pressure sensor, a temperature sensor, a capacitance sensor, and a conductance sensor.

In an example aspect combinable with any other example aspect, the venturi is vertically oriented by the coiled tubing assembly in the wellbore.

In an example aspect combinable with any other example aspect, the venturi is positioned such that all the multi-phase reservoir fluid flows through the venturi in the coiled tubing assembly.

In an example aspect combinable with any other example aspect, the production condition includes one or more of a water-in-liquid ratio a gas volume fraction.

In an example aspect combinable with any other example aspect, the controller performs operations including, based on the production condition, determining a production flow rate, the production flow rate includes at least one of an oil flow rate, a water flow rate, or a gas volume flowrate.

In an example aspect combinable with any other example aspect, the wellbore production system includes a power source to supply electrical power to the miniature multi-phase flowmeter.

Although the present implementations have been described in detail, it should be understood that various changes, substitutions, and alterations can be made hereupon without departing from the principle and scope of the disclosure. Accordingly, the scope of the present disclosure should be determined by the following claims and their appropriate legal equivalents.

The invention claimed is:

1. A method comprising:

in a wellbore formed in the Earth and extending to a hydrocarbon reservoir containing a multi-phase reservoir fluid, wherein a coiled tubing assembly comprising a multi-phase flowmeter having a venturi oriented in along a longitudinal axis of the coiled tubing assembly is deployed in the wellbore:

passing grease into the venturi from an outer surface of the multi-phase flowmeter through a greasing port extending into a void of the venturi, thereby lubricating the venturi;

conducting, by the coiled tubing assembly, the multi-phase reservoir fluid from the wellbore to the multi-phase flowmeter;

sensing, by the venturi and a plurality of sensors of the multi-phase flowmeter, a plurality of conditions of the multi-phase reservoir fluid, the plurality of conditions including a pressure, a differential pressure, a temperature, a bulk fluid flow rate, an electrical capacitance, and an electrical conductance of the multi-phase reservoir fluid; and determining, based on the plurality of conditions of the multi-phase reservoir fluid, a production condition of the hydrocarbon reservoir.

2. The method of claim 1, wherein determining the production condition of the multi-phase reservoir fluid by the electrical conductance comprises:

determining a permittivity of the multi-phase reservoir fluid;

comparing the permittivity of the multi-phase reservoir fluid to a threshold oil permittivity threshold, a water permittivity threshold, and a gas permittivity threshold; and based on a result of the comparison, determining the electrical conductance of the multi-phase reservoir fluid.

3. The method of claim 1, wherein the production condition comprises one or more of a water-in-liquid ratio or a gas volume fraction.

4. The method of claim 1, further comprising, based on the production condition, determining a production flow rate.

5. The method of claim 4, wherein the production flow rate comprises at least one of an oil flow rate, a water flow rate, or a gas volume flowrate.

6. The method of claim 1, further comprising:

transmitting values representing the plurality of conditions of the multi-phase reservoir fluid to a controller on a surface of the Earth; and receiving the values representing the plurality of conditions of the multi-phase reservoir fluid at the controller.

7. The method of claim 1, further comprising supplying electrical power to the multi-phase flowmeter.

8. The method of claim 1, further comprising orienting the multi-phase flowmeter in the wellbore such that the multi-phase reservoir fluid flows through the multi-phase flowmeter in a vertical direction relative to a surface of the Earth.

9. A wellbore production system comprising:

a wellhead coupled to a wellbore fluidly coupled to a hydrocarbon reservoir containing a multi-phase reservoir fluid;

a coiled tubing assembly configured to extend through the wellhead into the wellbore and flow the multi-phase reservoir fluid from the wellbore to a surface of the Earth;

a multi-phase flowmeter coupled to the coiled tubing assembly and positionable in the wellbore by the coiled tubing assembly, the multi-phase flowmeter comprising a venturi oriented in along a longitudinal axis of the coiled tubing assembly, the multi-phase flowmeter comprising a greasing port extending from an outer surface of the multi-phase flowmeter into a void of the venturi, the void extending along the longitudinal axis of the multi-phase flowmeter, the multi-phase flowmeter configured to:

sense a plurality of conditions of the multi-phase reservoir fluid, the plurality of conditions including a pressure, a differential pressure, a temperature, a bulk fluid flow rate, an electrical capacitance, and an electrical conductance of the multi-phase reservoir fluid; and transmit a signal representing the plurality of conditions of the multi-phase reservoir fluid; and a controller configured to perform operations comprising:

receiving a signal representing the plurality of conditions of the multi-phase reservoir fluid from the multi-phase flowmeter; and determining, based on the plurality of conditions of the multi-phase reservoir fluid, a production condition of the hydrocarbon reservoir.

10. The wellbore production system of claim 9, wherein the multi-phase flowmeter comprises at least one of a pressure sensor, a differential pressure sensor, a temperature sensor, a capacitance sensor, and a conductance sensor.

11. The wellbore production system of claim 10, wherein the venturi is vertically oriented by the coiled tubing assembly in the wellbore.

12. The wellbore production system of claim 10, wherein the venturi is positioned such that all the multi-phase reservoir fluid flows through the venturi in the coiled tubing assembly.

13. The wellbore production system of claim 9, wherein the production condition comprises one or more of a water-in-liquid ratio or a gas volume fraction.

14. The wellbore production system of claim 9, wherein the controller is further configured to perform operations comprising, based on the production condition, determining a production flow rate, the production flow rate comprising at least one of an oil flow rate, a water flow rate, or a gas volume flowrate.

15. The wellbore production system of claim 9, further comprising a power source configured to supply electrical power to the multi-phase flowmeter.

* * * * *